(12) United States Patent
Feinberg et al.

(10) Patent No.: US 10,150,258 B2
(45) Date of Patent: Dec. 11, 2018

(54) ADDITIVE MANUFACTURING OF EMBEDDED MATERIALS

(71) Applicant: CARNEGIE MELLON UNIVERSITY, Pittsburgh, PA (US)

(72) Inventors: Adam Feinberg, Pittsburgh, PA (US); Thomas Hinton, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 103 days.

(21) Appl. No.: 14/908,637

(22) PCT Filed: Jul. 29, 2014

(86) PCT No.: PCT/US2014/048643
§ 371 (c)(1),
(2) Date: Jan. 29, 2016

(87) PCT Pub. No.: WO2015/017421
PCT Pub. Date: Feb. 5, 2015

(65) Prior Publication Data
US 2016/0167312 A1     Jun. 16, 2016

Related U.S. Application Data

(60) Provisional application No. 61/958,484, filed on Jul. 29, 2013.

(51) Int. Cl.
*B29C 64/106*   (2017.01)
*A61L 27/38*   (2006.01)
(Continued)

(52) U.S. Cl.
CPC .......... *B29C 67/0092* (2013.01); *A61L 27/04* (2013.01); *A61L 27/10* (2013.01);
(Continued)

(58) Field of Classification Search
None
See application file for complete search history.

(56) References Cited

U.S. PATENT DOCUMENTS

2002/0195747 A1* 12/2002 Hull ........................ B29C 41/12
                                                           264/401
2006/0193769 A1   8/2006 Nelson et al.
(Continued)

FOREIGN PATENT DOCUMENTS

WO   WO2015/017421   2/2015

OTHER PUBLICATIONS

Golden et al., "Fabrication of Microfluidic Hydrogels Using Molded Gelatin as a Sacrificial Element", Lab on a Chip, vol. 7, No. 6, 2007, pp. 720-725.*

(Continued)

*Primary Examiner* — Jacob T Minskey
*Assistant Examiner* — Baileigh Kate Darnell
(74) *Attorney, Agent, or Firm* — Fish & Richardson P.C.

(57) ABSTRACT

In one aspect, a method includes providing support material within which the structure is fabricated, depositing, into the support material, structure material to form the fabricated structure, and removing the support material to release the fabricated structure from the support material. The provided support material is stationary at an applied stress level below a threshold stress level and flows at an applied stress level at or above the threshold stress level during fabrication of the structure. The provided support material is configured to mechanically support at least a portion of the structure and to prevent deformation of the structure during the fabrication of the structure. The deposited structure material is suspended in the support material at a location where the structure material is deposited. The structure material com- (Continued)

prises a fluid that transitions to a solid or semi-solid state after deposition of the structure material.

27 Claims, 12 Drawing Sheets

(51) Int. Cl.

| | |
|---|---|
| *B33Y 10/00* | (2015.01) |
| *B29C 67/00* | (2017.01) |
| *B29C 64/40* | (2017.01) |
| *B29C 64/112* | (2017.01) |
| *A61L 27/52* | (2006.01) |
| *A61L 27/04* | (2006.01) |
| *A61L 27/10* | (2006.01) |
| *A61L 27/14* | (2006.01) |
| *A61L 27/18* | (2006.01) |
| *A61L 27/20* | (2006.01) |
| *A61L 27/22* | (2006.01) |
| *A61L 27/24* | (2006.01) |
| *B33Y 70/00* | (2015.01) |
| *B29L 31/00* | (2006.01) |

(52) U.S. Cl.
CPC ............. *A61L 27/14* (2013.01); *A61L 27/18* (2013.01); *A61L 27/20* (2013.01); *A61L 27/22* (2013.01); *A61L 27/222* (2013.01); *A61L 27/225* (2013.01); *A61L 27/227* (2013.01); *A61L 27/24* (2013.01); *A61L 27/38* (2013.01); *A61L 27/52* (2013.01); *B29C 64/106* (2017.08); *B29C 64/112* (2017.08); *B29C 64/40* (2017.08); *B29C 67/0055* (2013.01); *B29C 67/0059* (2013.01); *B33Y 10/00* (2014.12); *B29K 2005/00* (2013.01); *B29K 2089/00* (2013.01); *B29L 2031/7532* (2013.01); *B33Y 70/00* (2014.12)

(56) References Cited

U.S. PATENT DOCUMENTS

| | | | |
|---|---|---|---|
| 2008/0109070 A1 | 5/2008 | Wagner et al. | |
| 2008/0145639 A1 | 6/2008 | Sun et al. | |
| 2010/0158976 A1 | 6/2010 | O'Brien et al. | |
| 2010/0179667 A1 | 7/2010 | Day et al. | |
| 2011/0159272 A1 | 6/2011 | Yue et al. | |
| 2011/0212501 A1* | 9/2011 | Yoo ......................... | A61L 27/54 435/174 |
| 2016/0228611 A1* | 8/2016 | Castro .................... | A61L 27/48 |

OTHER PUBLICATIONS

Landers et al., "Rapid Prototyping of Scaffolds Derived from Thermoreversible Hydrogels and Tailored for Applications in Tissue Engineering", Biomaterials, vol. 23, 2010, pp. 4437-4447.*

Wu et al., "Omnidirectional Printing of 3D Microvascular Networks", Advanced Materials, vol. 23, Issue 24, 2011, pp. H178-H183.*

Khalil et al., Multi-nozzle Deposition for Construction of 3D Biopolymer Tissue Scaffolds. *Rapid Prototyping Journal* 11(1): 9-17, 2005. [retrieved on Oct. 17, 2014]. Retrieved from the Internet. <URL: http://www.pages.drexel.edu/~sunwei/WSUN-Papers/RP-Multl-Nozzle-paper.pdf>. entire Document.

Lee et al., On-Demand Three-Dimensional Freeform Fabrication of Multi-Layered Hydrogel Scaffold With Fluidic Channels. *Biotechnology and Bioengineering* 105(6): 1178-1186, 2010. [retrieved on Oct. 16, 2014]. Retrieved from the Internet. <URL: http://www.zen-bio.com/pubs/On%20Demand%20Three%20Dimensional%20Freeform.pdf>. entire document.

International Search Report and Written Opinion dated Nov. 14, 2014 for Int'l. Appln. No. PCT/US2014/048643 (13 pgs.).

Wang Q et al., "Biodegradable Colloidal Gels as Moldable Tissue Engineering Scaffolds," Advanced Materials 20,236 239 (2008).

Duoss, E.B. et al., "Sol-Gel Inks for Direct-Write Assembly of Functional Oxides," Advanced Materials 19:3485-3489 (2007).

Huang Y.C. et al., "Rapid formation of functional muscle in vitro using fibrin gels," Journal of applied physiology, 98(2):706-13 (2005).

Boontheekul T. et al., "Regulating myoblast phenotype through controlled gel stiffness and degradation," Tissue Engineering 13, 1431-1442 (2007).

Landers R. et al., Fabrication of soft tissue engineering scaffolds by means of rapid prototyping techniques. 7, 3107-3116 (2002).

Reiffel A.J. et al., High-fidelity tissue engineering of patient-specific auricles for reconstruction of pediatric microtia and other auricular deformities. PloS one 8:e56506, 2013.

Miller J.S. et al., "Rapid casting of patterned vascular networks for perfusable engineered three-dimensional tissues," Nature Materials 11:1-7, 2012.

Norotte C. et al, "Scaffold-free vascular tissue engineering using bioprinting," Biomaterials 30, 5910-7 (2009).

Wu W. et al., Omnidirectional printing of 3D microvascular networks. Advanced Materials 178-183 (2011).

Wu W. et al., Direct-write assembly of biomimetic microvascular networks for efficient fluid transport, Soft Matter 6,739 (2010).

Tasoglu S. et al, "Bioprinting for stem cell research," Trends in biotechnology 31, 10-9 (2013).

Huang G. et al., "Microfluidic hydrogels for tissue engineering," Biofabrication 3:012001, 2011.

Choi N.W. et al., "Microfluidic scaffolds for tissue engineering," Nature materials 6:908-15, 2007.

Huang N.F. et al., "Engineering of aligned skeletal muscle by micropatterning," American Journal of Translational Research, 2:43-55 (2010).

Nguyen et al., "Biomimetic model to reconstitute angiogenic sprouting morphogenesis in vitro," Proceedings of the National Academy of Sciences 110(17):6712-7, 2013.

Mitsuhashi N. et al., "BodyParts3D: 3D structure database for anatomical concepts," Nucleic acids research 37:D782-5 , 2009.

Schmidt C. et al., "Existence of a flat phase in red cell membrane skeletons," Science—New York . . . (1993).

Huh D. et al., "Reconstituting organ-level lung functions on a chip," Science 328(5986), 1662-8 (2010).

* cited by examiner

ADDITIVE MANUFACTURING OF EMBEDDED MATERIALS

CROSS-REFERENCE TO RELATED APPLICATION

This application is a § 371 National Stage Application of PCT/US2014/048643, filed Jul. 29, 2014, which, in turn, claims the benefit of priority under 35 U.S.C. § 119(e) to provisional U.S. Patent Application No. 61/958,484 filed Jul. 29, 2013, the entire contents of each of which are hereby incorporated by reference.

FIELD OF THE USE

The present disclosure relates to fabricating multi-dimensional structures.

BACKGROUND

Additive manufacturing (AM) of biological systems has the potential to revolutionize the engineering of soft structures, bioprosthetics, and scaffolds for tissue repair. While 3D printing of metals, plastics, and ceramics has radically changed many fields, including medical devices, applying these same techniques for the printing of complex and soft biological structures has been limited. The major challenges are (i) deposition of soft materials with elastic moduli of less than 100 kilopascal (kPa), (ii) supporting these soft structures as they are printed so they do not collapse, (iii) removing any support material that is used, and (iv) keeping cells alive during this whole process using aqueous environments that are pH, ionic, temperature, and sterility controlled within tight tolerances. Expensive bioprinters that attempt to address these challenges have been produced, but have yet to achieve results using soft hydrogels that are comparable to results achieved using commercial grade thermoplastic printers.

Some hydrogels are impossible to deposit in layers due to their tendency to flow or deform under steady-state loading. However, hydrogels are desirable materials for advanced biofabrication techniques because their structure underlies the function of complex biological systems, such as human tissue. 3D tissue printing (i.e., AM of tissues) seeks to fabricate macroscopic living composites of biomolecules and cells with relevant anatomical structure, which gives rise to the higher-order functions of nutrient transport, molecular signaling, and other tissue-specific physiology. Replicating the complex structures of tissues with AM requires true freeform fabrication, as tissues possess interpenetrating networks of tubes, membranes, and protein fibers that are difficult to fabricate using free-standing fused-deposition or photopolymerization techniques. Conventional AM techniques may not possess the level of spatial control necessary for freeform fabrication and rapid prototyping of soft tissues.

Recent advances in 3D tissue printing represent solutions to highly specific problems encountered in the AM of hydrogel materials, and are often limited to a specific application. For example, Fused Deposition Modeling (FDM) has been used to print avascular replicas of cartilaginous tissues as well as fugitive vasculatures, which can be used to cast a vascularized tissue. Similar to the powders used in Solid Freeform Fabrication (SFF), dynamic support materials have been developed to enable the fabrication of soft materials in complex spatial patterns without the need of printed supports. These semi-solid materials may be capable of supporting the fusion of cells and gels; however, the latter cases are limited and do not constitute true freeform fabrication. Indeed, the most successful methods for fabricating macroscopic biological structures in vitro rely on casting and not AM, as conventional AM techniques may not be sufficient to recreate true tissue complexity.

Many gels are ideal materials for biofabrication, because their structures underlie the function of complex biological systems, such as human tissues. The geometries of tissues may be difficult to recreate without techniques like Additive Manufacturing/3D printing, but the methods for 3D printing gels are limited. Many gels start as fluids and cannot be 3D printed without supports to prevent them from drooping or oozing. Conventional 3D printing techniques may not possess the level of control necessary for geometrically unrestrained 3D printing of gels and tissues. Attempts to print gels with FDM have yielded cartilage-like tissues as well as gels with simple networks of vessels, yet the results have been limited. Indeed, it is still easier and more effective to cast a tissue than it is to 3D print it, as conventional 3D printing techniques may not be sufficiently capable.

SUMMARY

The present disclosure describes a method for 3D printing gels referred to as Embedded Fusion Modeling (EFM), or Freeform Reversible Embedding of Suspended Hydrogels (FRESH). EFM is similar to FDM, but instead of depositing a material on top of previous depositions or supports, EFM embeds material near other embedded deposits inside an omnipresent support bath and relies on the triggered assembly or reorganization of the material using targeted heating, photopolymerization, crosslinking, slow reaction kinetics, or application of binders. For example, the support bath may provide divalent cations for crosslinking the printed material. For 3D printing techniques such as FDM, support materials are usually as stiff as the printed material and placed underneath or neighboring the print layers to prevent deformations. In EFM, the support material is everywhere, and the deposit is printed inside the support. The support bath is a non-newtonian fluid that allows for deposition of new material while maintaining a buoyant, physical support for already embedded deposits. When two embedded deposits are close enough, they fuse. After printing, the deposit can be removed from the support as a fully assembled construct.

In one aspect of the present disclosure, a method includes providing support material within which the structure is fabricated, depositing, into the support material, structure material to form the fabricated structure, and removing the support material to release the fabricated structure from the support material. The provided support material is stationary at an applied stress level below a threshold stress level and flows at an applied stress level at or above the threshold stress level during fabrication of the structure. The provided support material is configured to mechanically support at least a portion of the structure and to prevent deformation of the structure during the fabrication of the structure. The deposited structure material is suspended in the support material at a location where the structure material is deposited. The structure material comprises a fluid that transitions to a solid or semi-solid state after deposition of the structure material.

Implementations of the disclosure may include one or more of the following features. The support material may include a gel material. The support material may include a hydrogel material. The support material may include micronized particulates. The support material may include a thermo-reversible material. The structure material may include a material having an elastic moduli of less than 1 megapascal. The structure material may include at least one of a gel material that is different from the support material, a metal material, a ceramic material, or a polymer material. The structure material may include at least one of an alginate material, a collagen material, a fibrin material, a hyaluronic acid material, a protein material, a polysaccharide hydrogel material, synthetic gel material, an elastomer polymer material, a rigid polymer material, or a polydimethylsiloxane (PDMS) elastomer. The structure material may be deposited using a syringe-based extruder that is inserted into the support material and extrudes the structure material into the support material. The method may include treating the structure material to cause the structure material to transition from the fluid to the solid or semi-solid state after the deposition of the structure material. The support material may include a crosslinking agent for treating the structure material to cause the structure material to transition from the fluid to the solid or semi-solid state after the deposition of the structure material. The crosslinking agent may include at least one of calcium chloride or thrombin. The support material may include a material having a different pH from the structure material for treating the structure material to cause the structure material to transition from the fluid to the solid or semi-solid state after the deposition of the structure material. Treating the structure material may include heating the structure material, cooling the structure material, or radiating the structure material with ultraviolet light. Removing the support material may include heating the support material, cooling the support material, or removing cations to disrupt crosslinking of the support material. The fabricated structure may be a biological tissue or a tissue engineering scaffold. Depositing, into the support material, the structure material to form the fabricated structure can include depositing the structure material layer by layer in an XY plane, depositing the structure material layer by layer in an XZ plane, or depositing the structure material in a non-planar configuration.

In another aspect of the present disclosure, a method includes performing a printing operation at approximately twenty degrees Celsius. The printing operation may include providing a gelatin slurry support bath within which the tissue scaffold is fabricated, extruding, from a nozzle, a hydrogel into the gelatin slurry support bath to form the tissue scaffold, and placing the gelatin slurry support bath with the extruded hydrogel into an incubator that is heated to approximately thirty-seven degrees Celsius to melt the gelatin slurry support bath and to release the tissue scaffold. The hydrogel has an elastic moduli of less than 1,000 kilopascal. The gelatin support bath flows in a presence of an applied force and transforms into a non-flowing fluid in an absence of the applied force. The gelatin slurry support bath includes calcium chloride to provide divalent cations to crosslink the hydrogel as the hydrogel is extruded out of the nozzle. The gelatin slurry support bath is configured to mechanically support the hydrogel and to prevent deformation of the hydrogel during printing of the tissue scaffold.

Implementations of the disclosure may include one or more of the following features. The hydrogel may include at least one of alginate, collagen type I, fibrin, or hyaluronic acid. The hydrogel may include a cell laden hydrogel.

Particular implementations of the subject matter described in this disclosure may be implemented to realize one or more of the following potential advantages. The 3D printing techniques described in this disclosure are applicable to gelling polymers and enable true freeform printing of complex geometries. The techniques can be used to produce anatomically correct, perfusable scaffolds of coronary arteries. The techniques are cross-platform and can easily be adopted for use on many open-source and proprietary 3D printers.

Details of one or more implementations are set forth in the accompanying drawings and the description below. Other features, objects, and advantages will be apparent from the description, the drawings, and the claims.

DETAILED DESCRIPTION

Figure 1:
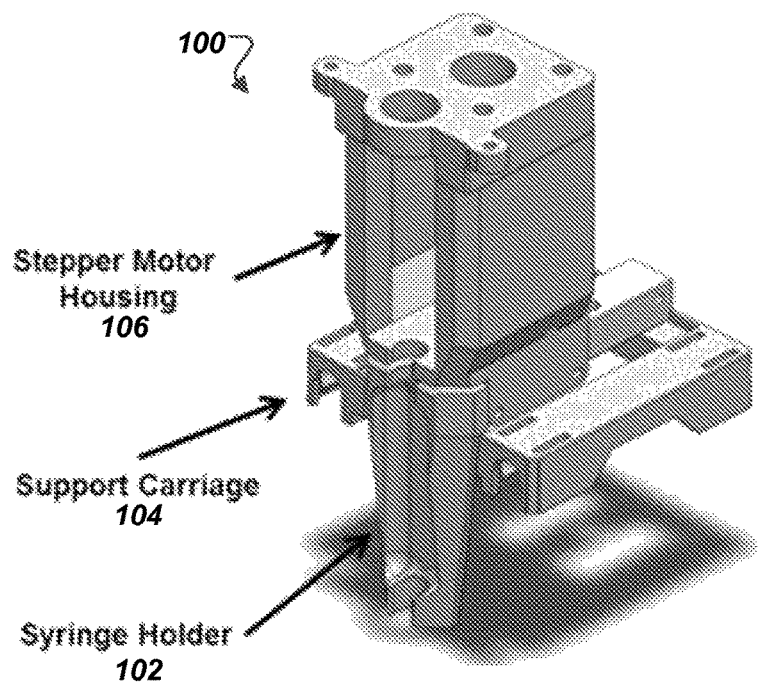
FIG. 1 shows a 3D CAD rendering of a syringe-pump extruder.

Although the techniques described in the present disclosure are applicable to a wide range of manufacturing processing methods, various implementations will be described below in the context of additive manufacturing. While specific implementations are described, other implementations may exist that include operations and components different than those illustrated and described below.

The present disclosure describes a method of embedding fused materials (EFM) within a support bath, where the embedded material is initially a fluid or flowable material that transitions to a solid or semi-solid state after deposition. The method can be used in the process of additive manufacturing (AM), also commonly referred to as freeform fabrication or 3D printing, of soft materials to fabricate 2D or 3D structures and objects based on a 3D digital design, which may be difficult using traditional techniques or current additive manufacturing approaches. While specific examples of soft materials and their characteristics are provided below, EFM is not limited to printing materials with a specific material hardness and other materials with different characteristics may be printed.

The soft materials can include fluids that have substantially low elastic modulus when being printed. Traditionally, printing a fluid in air may be difficult because the fluid may flow away from the deposition site.

The soft materials can include solid materials that have an elastic modulus in the range of approximately 10 GPa to 0.1 kPa. These solid materials may sag or deform if printed in air. For example, stiff materials such as cements, resins, and concretes can be printed using EFM. Composites involving metal-ceramic or metal-carbon alloys can also be printed using EFM.

The soft materials can include materials that have an elastic modulus that is initially low and increases over time due to crosslinking or assembly of the material. The final elastic modulus of these materials may be in the GPa range after crosslinking or assembly, but may be difficult to print using other techniques because the elastic modulus was much lower during the print process. An example of such materials include an epoxy resin that is mixed but has not yet cured, so it is a liquid during printing but then cures overtime into a rigid plastic. Another example is a polydimethylsiloxane (PDMS) elastomer (e.g., Sylgard 184, Dow Corning) that can be mixed as a prepolymer, printed as a liquid, and then cured for 48 hours at room temperature while still immobilized in the gelatin slurry support material before being released at 37 degrees Celsius.

The soft materials are printed inside a temporary support material that can be removed later by, e.g., heating or cooling the support material to dissolve or melt the support material, or removing cations to disrupt crosslinking of the support material. Additional techniques for removing the support material include vibration, irradiation with ultraviolet, infrared, or visible light, or application of a constant or oscillating electric or magnetic field.

The support material may be any material that acts as a viscoplastic material with Bingham plastic-like rheological behavior. The support material may demonstrate a significant shear thinning behavior such that the support material acts like a solid material during deposition of the structure materials and then acts like a fluid when the nozzle is moved through the support material such that the nozzle movement does not disturb the deposited structure material. The support material may exhibit viscoplastic behavior where it acts as a solid below a threshold shear stress and flows like a liquid above the threshold shear stress. The characteristic that makes a support material suitable for EFM is a drop in viscosity under dynamic loading. In EFM, the dynamic loading is caused by the force of an extruder moving through the support material, affecting the support material in a number of ways. The extruder could change the support material by imposing a mechanical load via shear, pressure, or vibration. The extruder could irradiate or heat the support material to thin it. Alternatively, a suitable material could lose viscosity under vibration, heating, or irradiation that occurs locally to the extruder.

For example, the support material can include a Bingham plastic, or Bingham plastic-like, material that is a solid material when not perturbed, but shear thins and provides minimal resistance when a nozzle moves through it. The support material can include other materials with viscoplastic behavior, such as Herschel-Bulkley fluid. Bingham plastics and Herschel-Bulkley fluids are viscoplastic materials included in the "shear-thinning" or "yield-stress fluid" category. Below a specific shear stress, these materials appear as a solid material. Above a threshold shear force, these materials behave as a fluid. A Bingham plastic may not necessarily "shear thin," but rather may act much like a Newtonian fluid once it begins to flow. In contrast, the Herschel-Buckley fluid undergoes shear thinning once it begins to flow.

Thus, a 3D bioprinter can lower a syringe-based extruder into the support material and move around and deposit material in arbitrary 3D geometries. The extruded material stays in place once the tip of the extruder moves away, thus forming the 3D printed object. Once the complete 3D object is printed and the structural material has sufficiently assembled, the support material is removed.

A structure can be printed in any direction in 3D space. In addition to the typical 3D printing that is done layer by layer in the XY plane, a structure can also be printed layer by layer in a non-XY plane, such as the XZ plane, or a plane at any angle. A structure can also be printed in a non-planar fashion in a curved path, such as a helix. Structures with material mechanical properties that are different in the plane of printing versus orthogonal to the plane of printing can thus be printed using EFM. In particular, the fabricated structured can have three-dimensions, and the fabricated structure can have printed anisotropic mechanical properties in a direction that lie in XY plane. For example, EFM can be used to print in the direction of nerve fibers in 3D, or in the direction of muscle fibers in 3D.

Some AM techniques rely on the triggered assembly or reorganization of a material using targeted heating, photopolymerization, or jetted glues to bind a powder substrate. EFM is more similar to Fused Deposition Modeling (FDM), but in FDM, material is deposited on top of a previously deposited layer, which provides the necessary mechanical support to build multiple layers since this process occurs in an environment with no buoyant or conformal supports and requires the co-printing of supporting structures. In contrast, EFM deposits material near previously deposited material, but not necessarily on top of it. Specifically, the support bath material provides mechanical support with the deposited, embedded materials able to fuse in any direction as long as proximity is sufficient. To accomplish this, fusible material is deposited into the support bath material, which behaves as a buoyant, non-Newtonian support. Support materials are usually as stiff as the intended deposit and placed underneath or neighboring the deposit to prevent deformation of the deposit. In EFM, the support material is everywhere, and the deposit is embedded inside the support material during printing. After printing, the object can be removed from the support as an intact object.

EFM can print any fluid that transitions to a solid or semi-solid state after deposition. Examples of materials which can be manufactured using EFM are ceramics, metals, polymers, sol-gel mixtures, composites, and gels. Concretes, cements, clays, slurries and colloids of metals and metallic or semi-metallic oxides, epoxies, resins, silicones, and thermoplastics can all be assembled using EFM. Additionally, EFM is also capable of 3D printing gels made from proteins, polysaccharides, or other polymers and stable hydrocolloids.

Additionally, foods such as Nutella, mayonnaise, or chocolate, and adhesives such as cyanoacrylates can also be assembled using EFM. EFM can also be used to print biologically derived protein and/or polysaccharide hydrogels such as chitosan or Matrigel, synthetic hydrogels such as polyethylene glycol (PEG) based hydrogels, and other synthetic gel, elastomer and rigid polymers such as polydimethylsiloxane, polyurethanes, thermosets, coacervate solids, and foams.

Support materials used in EFM can include any slurry or fluid exhibiting properties which allow it to support the embedding of a fusible material. Some examples of support materials are mayonnaise, albumin-foams, gelatin slurries, poly(N-isopropylacrylamide) (PNIPAAM) slurries, polyacrylate slurries, alginate slurries, and structured fluids displaying non-newtonian, Bingham Plastic behaviors, or other viscoplastic materials such as Herschel-Bulkley fluid. Conditions inside the support materials could be used to trigger the transition of the embedded material from fluid to solid or semi-solid state.

For example, a ceramic slurry consisting of an aggregate material surrounded by a suspension of hydrating minerals can be deposited into a pseudofluid slurry. This enables the printing of cement-like or colloidal ceramics into complex shapes without the need for a powder & binder-based printing process. Additionally, a Bingham plastic oil-in-water emulsion could be used as a support material.

In some implementations, a 3D printing technique referred to as Freeform Reversible Embedding of Suspended Hydrogels (FRESH) to enable the 3D printing of soft, biological hydrogel structures that may be too soft to fabricate using other 3D printing techniques. The structures may be any 3D design including anatomical structures in humans or the target organism for the object, such as the tissue engineering of an organ. FRESH enables true freeform printing of complex geometries and enables the geometrically uninhibited fabrication of biopolymers and cell suspensions by embedding them in thermo-reversible support material. FRESH printing may be a significant improvement over alternative 3D bioprinting approaches in terms of capability, cost, safety, speed, and ease of use. FRESH is cross-platform, and can therefore be easily adopted for use on an open-source or proprietary FDM 3D Printer.

FRESH uses a support bath material that enables biological hydrogels to be directly printed in 3D complexity using a range of soft biomaterials including alginate, collagen, hyaluronic acid, and fibrin. The thermo-reversible support bath may be composed of microparticles that act as a Bingham plastic or Herschel-Buckley fluid during the print process. As a nozzle moves through the bath, it shear thins and offers little mechanical resistance, yet the hydrogel being extruded out of the nozzle and deposited within the bath is held in place. The nozzle of the extruder moves through the support material fast enough such that the nozzle generates a shear stress above a threshold shear force and therefore sees the support material as a fluid. In contrast, the structure material deposited by the extruder out of the nozzle has a shear stress below the threshold shear force and therefore sees the support material as a solid material, and thus stays where it is deposited. Thus, soft materials that would collapse if printed in air or other bath materials are easily maintained in the intended 3D geometry. The process is performed in a sterile aqueous, buffered environment compatible with cells, which means cells can be extruded out of the printer nozzle with the hydrogel and maintain viability. Once the entire 3D structure is FRESH printed, the thermo-reversible property of the support bath material can be used to melt out the support bath at a cell-friendly 37° C., completely removing the support in a non-destructive manner.

A range of materials using FRESH have been 3D printed, including alginate, collagen, fibrin, matrigel, photo-crosslinkable hyaluronic acid, cell suspension in collagen, and PDMS, which is a non-hydrogel. A wide range of 3D objects have been printed including geometric solids, vascular networks, whole organs such as the embryonic heart, and intricate scaffolds. FRESH can be used to tissue engineer a range of tissue types, including, for example, cardiac muscle tissue for the repair of congenital heart defects and myocardial infarction, vascular networks for the repair/regeneration of skeletal muscle tissue, and high-fidelity tissue engineering of skeletal muscle for craniofacial repair. The possibilities can extend beyond muscular tissues, potentially allowing for any known tissue type, including precursor embryonic tissues. The engineered tissues created using FRESH can be used in vitro models of tissue/organ function and/or as disease model systems.

FRESH may be used to 3D print biological tissues and tissue engineering scaffolds for application in regenerative medicine. A thermoreversible, Bingham plastic slurry supports the embedding, assembly, and release of a gelling polymer. In turn, conditions inside the slurry could be used to trigger the polymerization of the printed material. For the slurry, gelatin may be used in a calcium-rich solution, and for the gelling polymer, alginate may be used. However, FRESH is not limited to these materials. FRESH can be expanded to include any Bingham plastic or Herschel-Buckley fluid support material. Additionally, any gelling biomaterial or organogel can be used as an ink. Depending on the ink, any reversible gel can be used as a support, for example, alginate gels, collagen gels, PNIPAAM, or an organogel.

Using FRESH, perfusable scaffolds of coronary vasculatures can be fabricated using public-access MRI data, for example, open-source softwares such as Skeinforge and ReplicatorG, and an open-source MakerBot 3D printer. For example, FRESH can be used to produce anatomically correct, perfusable scaffolds of coronary arteries. Scaffolds with this range of mechanical properties are required for the tissue engineering of soft tissues. In one example, alginate or proteinaceous scaffolds composed of various geometries can be 3D printed in a support material. The support material may be a gelatin slurry in the form of micronized particulates. The support material is placed in a support bath supplemented with calcium chloride ($CaCl_2$). Alginate scaffolds are then 3D printed within the support bath, where the calcium ions crosslink the alginate and the gelatin mechanically supports the alginate. Once the alginate scaffolds are printed, the gelatin is melted by heating the gelatin to its melting temperature (37° C.) and then removed by washing it out.

While the above example demonstrates FRESH using alginate crosslinked by calcium chloride in the support bath, alginate is just one example of the embedded material. For example, the alginate can be modified with covalently grafted polypeptides to add additional biofunctionality such as adhesion sites for integrins or degradation sites that can be cleaved by matrix metalloproteinases. The alginate can also be blended with other polymers such as collagen or fibrin. Instead of alginate, fibrin can be printed by putting fibrinogen in the extruder and then use the calcium chloride in the bath and/or thrombin in the support bath to crosslink the fibrinogen into fibrin. Another example is printing collagen type I. The collagen I may be in a slightly acidic solution to prevent polymerization. The collagen type I is placed in the syringe and printed in a gelatin bath. The gelatin bath has a neutral pH, which triggers gelation of the collagen I. After printing, the bath is heated to 37° C., which simultaneously provides additional crosslinking of the collagen and melts the gelatin. As an alternative to heating, photochemistry may be used to crosslink the embedded material. For example, photocrosslinkable hyaluronic acid can be printed in the support bath, and UV light applied during the print process and/or afterwards is used to crosslink the hyaluronic acid into a hydrogel. There are multiple comparable examples of embedded soft materials and using various factors (e.g., heat, enzymes, light) to trigger transition of the printed material from a fluid into a gel or stiffer materials. Factors that trigger transition of the printed material can include, e.g., chemical exposure, vibration, radiation using ultraviolet, infrared, or visible light, and application of a magnetic or electric field.

While the above example describes the support bath as a gelatin particulate slurry that acts as a Bingham plastic-like material, there are a wide range of other materials that can be used to create the support bath. For example, instead of gelatin, ultra-low melting point Agarose can be used in a similar manner, where particulates are formed and used to make a slurry. The Agarose has a similar thermo-reversible characteristic to gelatin and thus can be melted at physiologic temperatures. Other forms of Agarose with higher melting temperatures could be used for print materials with different thermal properties.

FRESH printing can be implemented using a 3D printer based on open-source designs, or commercially available derivatives. For example, a fab@home model 2 3D printer comes with a syringe-based tool that can extrude soft materials. The fab@home is a widely used syringe-based printer for soft materials with examples of the printer being used to create alginate heart valves, silicone chemical reaction vessels, and even a bionic ear.

As another example, a RepRap derivative printer, which has a large array of open-source tools, is used. The stock MakerBot uses fused filament fabrication (FFF) where a thermoplastic filament (typically ABS or PLA) is fed into a heated chamber, melted, and then extruded before it cools and solidifies. This process may not work for hydrogels because they are too soft (flexible) to be used in filament extrusion. A syringe extruder is available on the MakerBot, termed the Frostruder, and a variant is used to 3D print sugar scaffolds that could be used to template vascular networks. However, the large volume of the syringe and pneumatic control may not provide the desired level of control. A syringe-pump based extruder may be designed on Solid-Works where the stepper motor from the original extruder is used via a direct gear drive to push the plunger of a syringe with Luer lock tip. The syringe-pump extruder was 3D printed of PLA or ABS plastic using the MakerBot's stock FFF extruder. The FFF extruder was then replaced with the syringe-pump extruder, converting the MakerBot into a bioprinter.

FIG. 1 shows a 3D CAD rendering of the syringe-pump extruder 100 showing the location where the syringe is mounted (syringe holder 102), where the support carriage 104 is that mounts to the MakerBot X-axis rails and the location where the stepper motor is housed (stepper motor housing 106). Note that the stock extruder is first used to print the syringe-pump extruder 100 in PLA or ABS plastic and then replaced. The overall design of the syringe-pump extruder 100 has similar mass and shape to the original stock extruder and once mounted integrates seamlessly with the MakerBot hardware and software. The only calibration necessary is to determine the number of motor steps that extrudes a given amount of fluid, which is determined experimentally for the alginate and collagen hydrogels printed. Typically, it places a 250 µm diameter stainless steel nozzle on the end of the syringe, but a range of sizes can be selected to control the diameter of extruded material.

Figure 2:
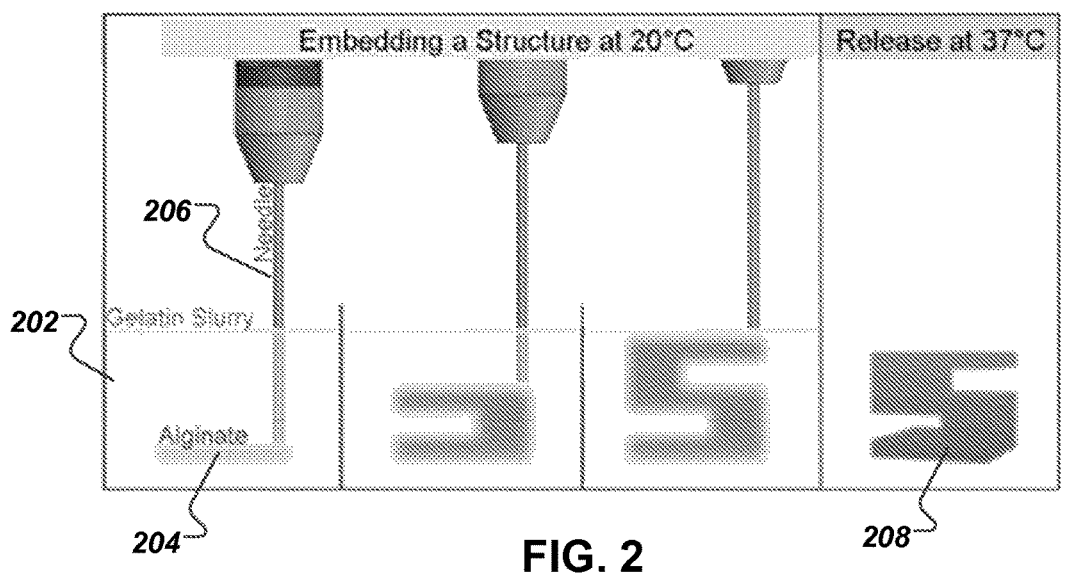
FIG. 2 shows printing of a soft hydrogel using a support bath.

FIG. 2 shows FRESH printing using a gelatin slurry as the thermo-reversible Bingham plastic support bath 202 and alginate 204 as the soft hydrogel being printed. The size of gelatin particles may interfere with alginate print topology, so gelatin slurries may be blended in a common blender, resulting in a narrower distribution of smaller particles. For example, slurries blended for 60 seconds were shown to have a dominant elastic behavior that is characteristic of a Bingham Plastic. $CaCl_2$ in the support bath 202 provides divalent cations to crosslink the alginate 204 as it is extruded out of the nozzle 206. The printing process occurs at room temperature (e.g., approximately 20° C.). Layers of deposited alginate gel, each representing a 2-dimensional slice of a 3D object, were built up by successive depositions to create a 3D scaffold. Once the printing is complete, the temperature is increased to 37° C. in order to melt the gelatin of the support bath 202 and release the embedded alginate structure 208.

Gelatin is selected as the material for the support bath 202 for the bioprinting of soft biological materials because it has many advantages including (i) inexpensive, (ii) biocompatible, (iii) thermo-reversible at physiologic temperatures, and (iv) readily available in a particulate form. Gelatin is a widely used biopolymer derived from collagen type I and normally is dissolved in warm water and then cooled down to form a crosslinked hydrogel. In this form, gelatin is not a Bingham plastic and will not work as the support bath 202. However, the gelatin powder as purchased can be added to room temperature (approximately 20° C.) water, and then the excess water can be drained off to form a gelatin particulate slurry. Alternatively, the gelatin slurry can be made by blending a block of gelatin gel in a jar with additional fluid. The result is a gelatin slurry that has gelatin particles with lower stiffness and greater transparency than the block of gelatin gel. However, any manner in which small gelatin gels can be fabricated can be used to make a gelatin slurry. For example, emulsion of warm gelatin solution in oil followed by cooling results in a gelatin microsphere suspension that can also be used as a support material.

The gelatin slurry behaves as a Bingham plastic, where the hydrated particulates act as a viscous fluid under the high stress of the extruder nozzle 206 moving through the bath 202 but a solid under low stress. 3D printing is done at room temperature to keep the gelatin as a solid, and alginate 204 is extruded into the slurry as the printed material. The support bath 202 is supplemented with $CaCl_2$ to provide divalent cations to crosslink the alginate 204 as it is extruded out of the nozzle 206. Once the 3D printing is complete, the bath 202 is heated to 37° C. in order to melt the gelatin and release the embedded alginate structure 208.

FRESH can be used to fabricate biological materials and structures. The gelatin slurry has an aqueous environment with neutral pH and physiological levels of $CaCl_2$. The temperature range is cell friendly, with most cells able to survive at room temperature for the printing process and at 37° C. for the thermal release. Initial studies printing C2C12 cells inside the alginate has shown greater than 97% cell survival using Live/Dead cell staining.

Figure 3A:
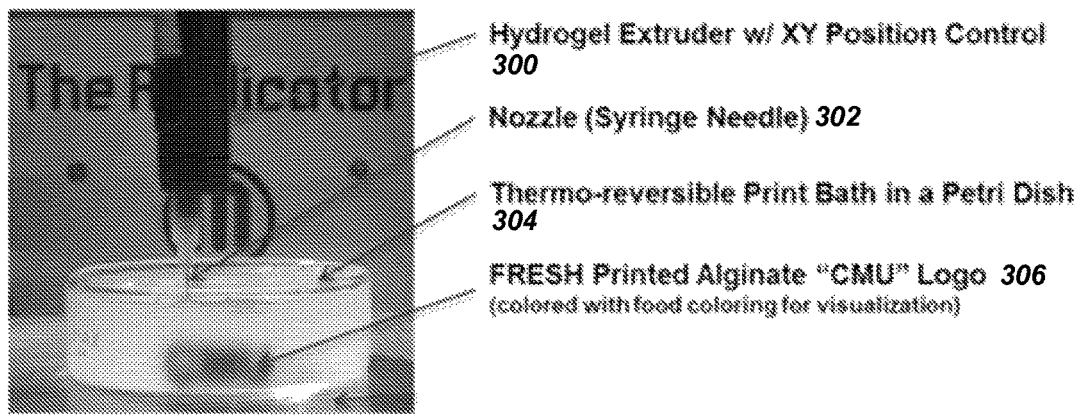
FIGS. 3A and 3B show printing using a 3D printer including an XY syringe-based extruder that deposits hydrogels from a nozzle into a thermo-reversible support bath.
Figure 3B:
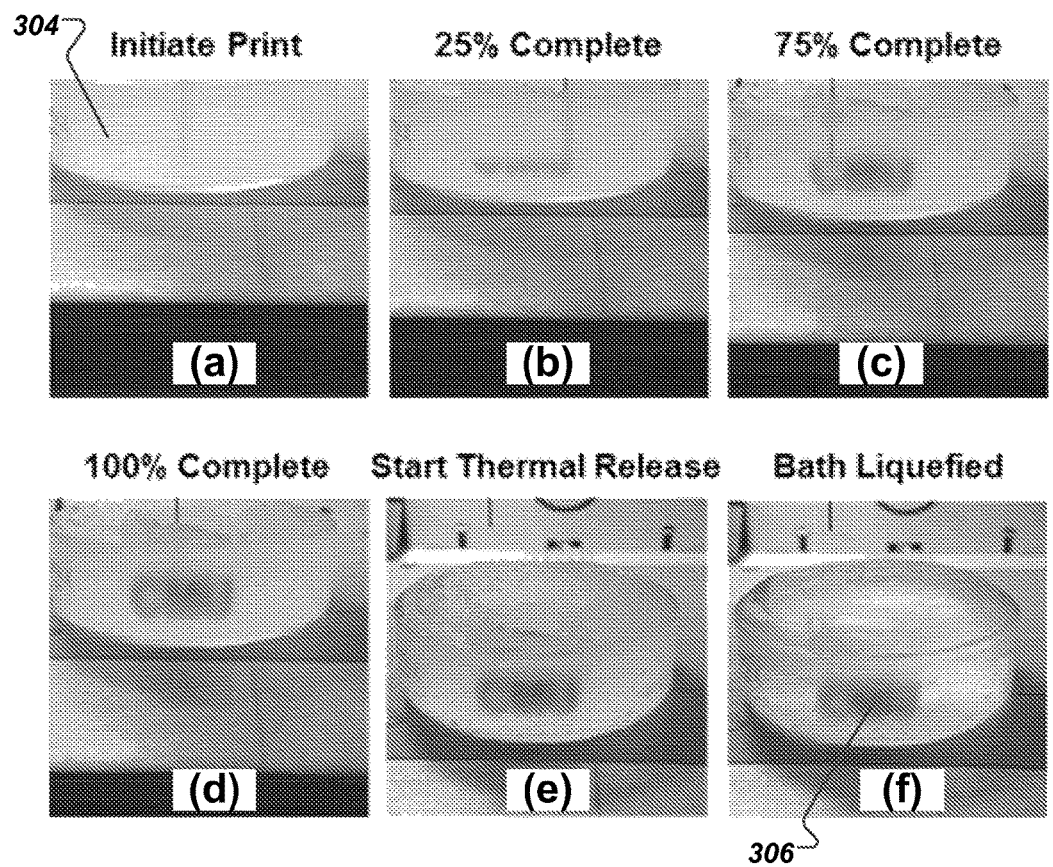

This system can print a large range of 3D objects including basic geometric solids, various 2D and 3D meshes, and anatomical structures based on medical imaging data. For example, FIGS. 3A and 3B show FRESH printing of the logo 306 using a 3D printer including an XY syringe-based extruder 300 that deposits hydrogels from a nozzle 302 into a thermo-reversible support bath 304. The FRESH printing process is based on using a thermo-reversible support bath 304 that can be removed after the printing process is completed. The support bath 304 needs to allow the nozzle 302 of the extruder 300 to move through the bath 304 with minimal resistance, but provide support to the extruded hydrogel. The support bath 304 may be achieved using a thermo-reversible Bingham plastic material, which is solid at low stresses and a viscous fluid at high stresses. The support bath 304 enables the embedding of a hydrogel during printing followed by non-destructive release when completed. The thermo-reversible support bath 304 may be composed of microparticles that act as a Bingham plastic during the print process.

As the nozzle 302 moves through the bath 304 it shear thins and offers little mechanical resistance, yet the hydrogel being extruded out of the nozzle 302 and deposited within the bath 304 is held in place. Thus, soft materials that would collapse if printed in air, or other bath materials, are easily maintained in the intended 3D geometry. Once the entire 3D structure is FRESH printed, the thermo-reversible property can be used to melt out the support bath 304 at a cell-friendly 37° C., completely removing the support bath 304 in a non-destructive manner. The printing is done in a sterile aqueous, buffered environment compatible with cells, which means cells can be extruded out of the printer nozzle with the hydrogel and maintain viability.

In FIGS. 3A and 3B, the logo 306 was printed in alginate in the gelatin slurry support bath 304. The alginate was mixed with food coloring to aid visualization during the printing process and various time points (a)-(d) show the layer-by-layer fabrication. The cloudiness of the bath is due to the particulate gelatin. As the nozzle of the extruder moves through the bath it disrupts the gelatin particles above the printing plane, but not below it. The logo 306 is printed in high fidelity at a 5 mm height, and even the overhang of the letter "C" is well formed and perfectly maintained using the support bath 304, which would be difficult to print with soft materials using other methods. Once the print is completed, the printing platform of the 3D printer is heated above 37° C. in time points (e) and (f) to melt the gelatin so the printed logo 306 can be removed from the bath 304. Note the surface of the bath 304 in the last time point (f) where the change from particles to liquid is visible.

Figure 4A:
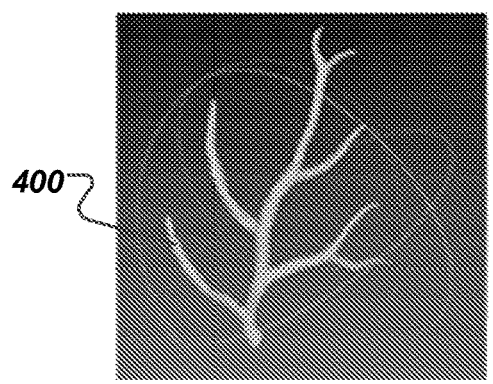
FIG. 4A shows a 3D CAD model of a coronary artery vasculature from a human heart.

Similarly, 3D models of the right coronary arterial tree from a human heart can be scaled-down and printed using FRESH with high fidelity. FIG. 4A shows a 3D CAD model 400 of the coronary artery vasculature from a human heart. Coronary artery 3D models based on whole-body MRI imaging can be downloaded from a database that has 3D data for major arteries and veins in the body. The right coronary arterial tree was downloaded and the hollow model 400 was created in MeshLab by resampling the solid model to create a smaller child model with inverted normals to serve as negative space. When the models are flattened as layers into the same mesh file, a hollow model 400 with internal and external surfaces results.

Figure 4B:
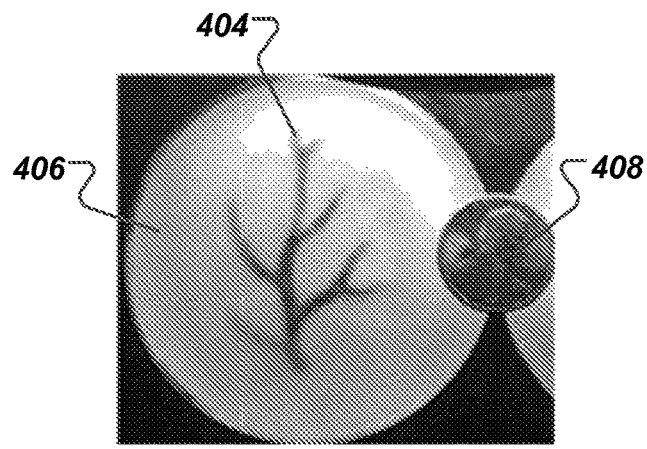
FIG. 4B shows a scaled-down print of the vasculature embedded within a support bath.
Figure 4C:
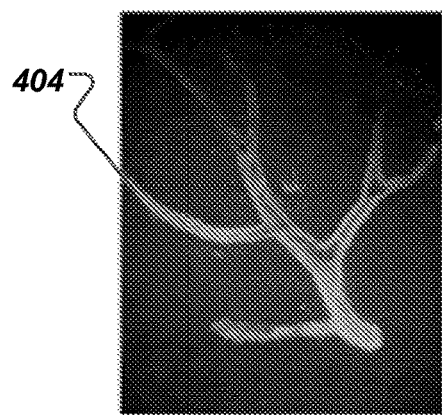
FIG. 4C shows the printed vasculature after thermal release from the support bath.

FIG. 4B shows a scaled-down FRESH printed vasculature 404 embedded within a support bath 406 with a US penny 408 for size reference. Using fluorescently-labeled alginate, the arterial tree was 3D printed with an internal luminal diameter of approximately 1 mm. The printed vasculature 404 can be released intact from the thermo-reversible support bath 406 and imaged using a laser scanning confocal microscope to visualize the hollow lumen that is generated. FIG. 4C shows the FRESH printed vasculature 404 after thermal release from the support bath 406 and imaged using a confocal microscope showing the hollow lumen with a diameter of approximately 1 mm. These scaffolds have been printed with 100% alginate a 50:50 mixture of alginate and collagen, pure collagen 1 solution, and pure fibrinogen solution.

Figure 5:
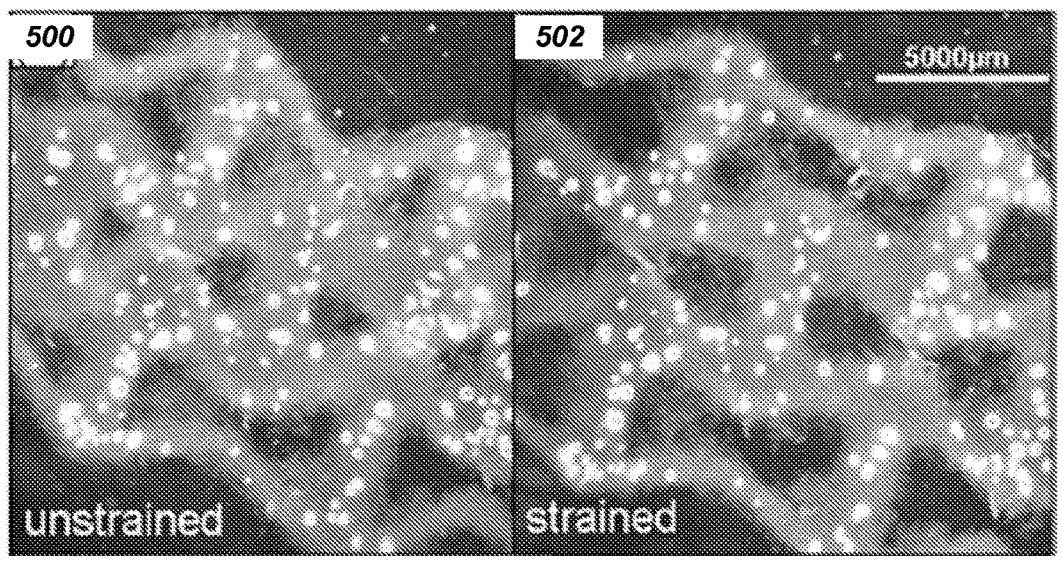
FIG. 5 shows a printed alginate mesh of collapsed hexagonal units exhibiting a negative Poisson's ration behavior when transitioning from an unstrained form to a strained form.
Figure 6:
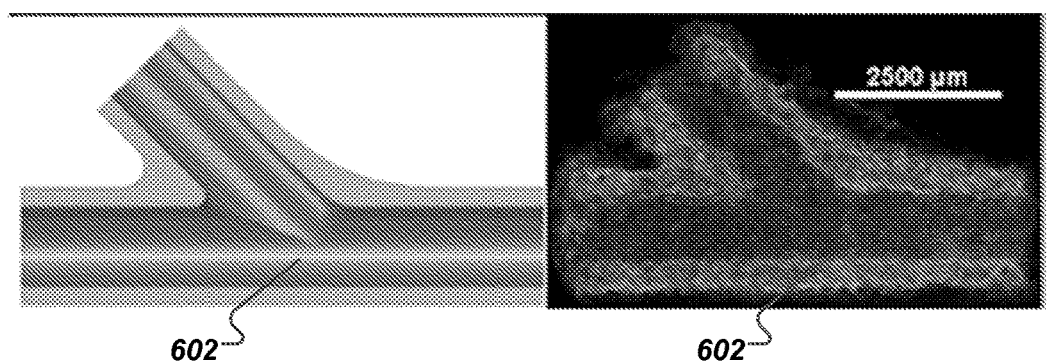
FIG. 6 shows a parametric tubular structure that was designed in CAD and printed.
Figure 7:
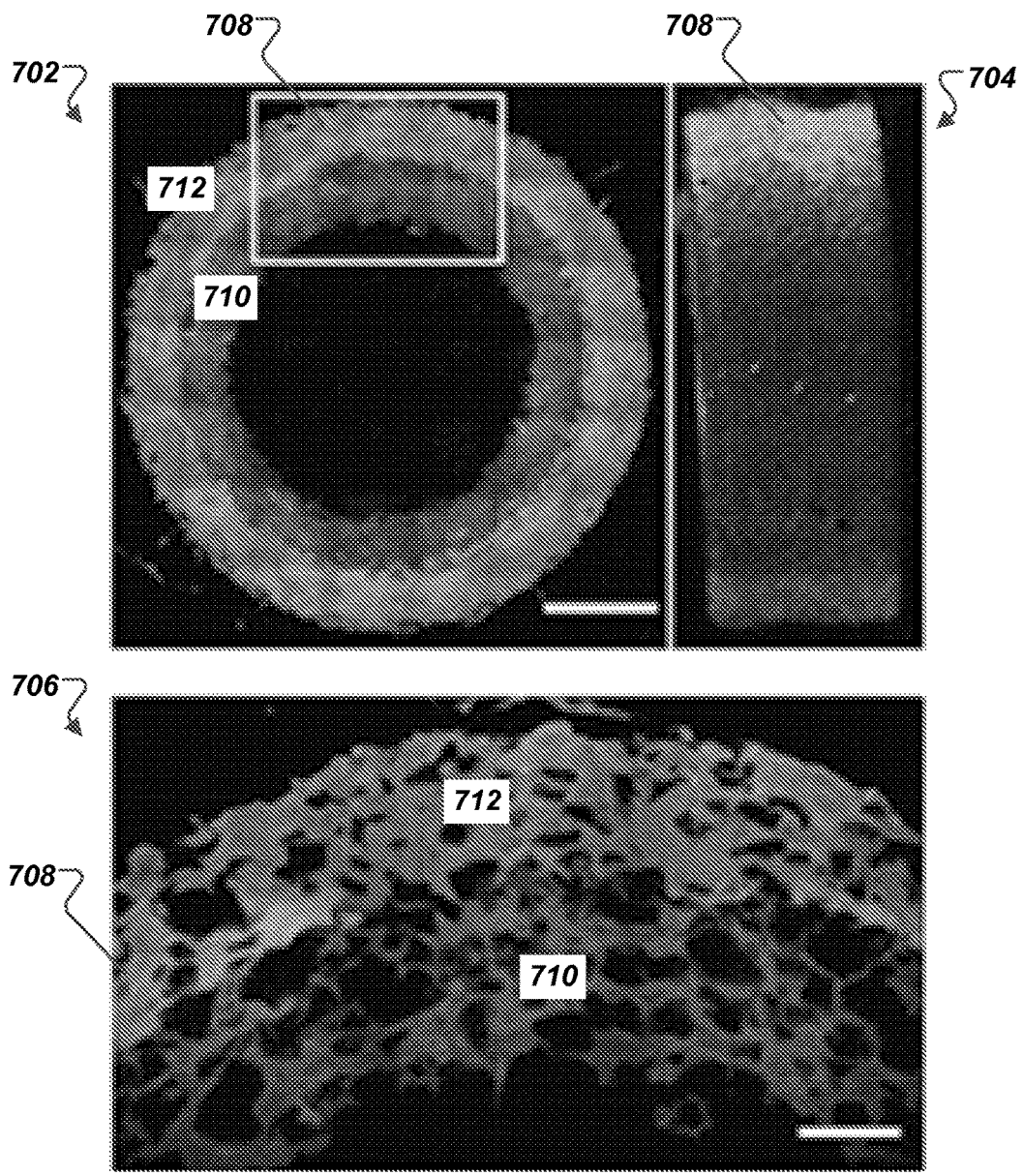
FIG. 7 shows a cross-section view, a side view, and a close-up cross-section view of a two-material cylinder.

Tubular and beam-like structures with simple mechanical behaviors can be compounded to print constructs with higher order functions. For example, solids with negative Poisson's ratios or hollow geometries can be printed. FIG. 5 shows a printed alginate mesh of collapsed hexagonal units in an unstrained form 500 and a strained form 502 under axial strain displaying transverse expansion, which indicates a negative Poisson's Ratio. FIG. 6 shows a parametric tubular structure 602 with a 2 mm inner diameter and bifurcation that was designed in CAD and printed, revealing a gel manifold capable of dividing fluid flow. FIG. 7 shows a cross-section view 702, a side view 704, and a close-up cross-section view 706 of a two-material cylinder with inner material 710 and outer material 712. The cross-section view 702 and the side view 704 are shown at a scale of 2 mm. The close-up cross-section view 706 is shown at a scale of 500 µm.

Figure 8:
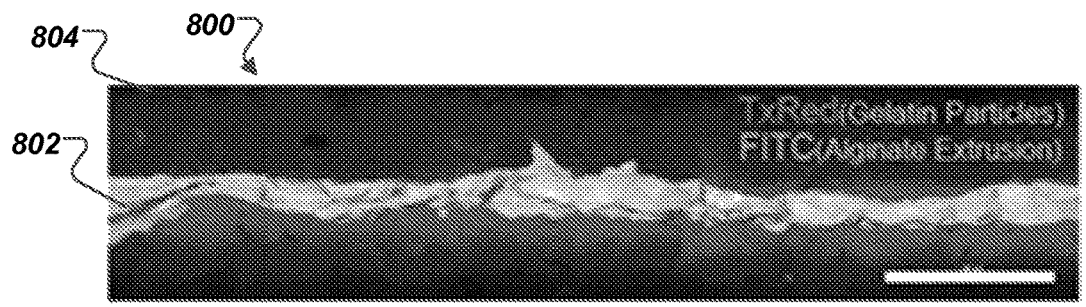
FIG. 8 shows a fluorescence image of an alginate filament embedded among gelatin particles.
Figure 9:
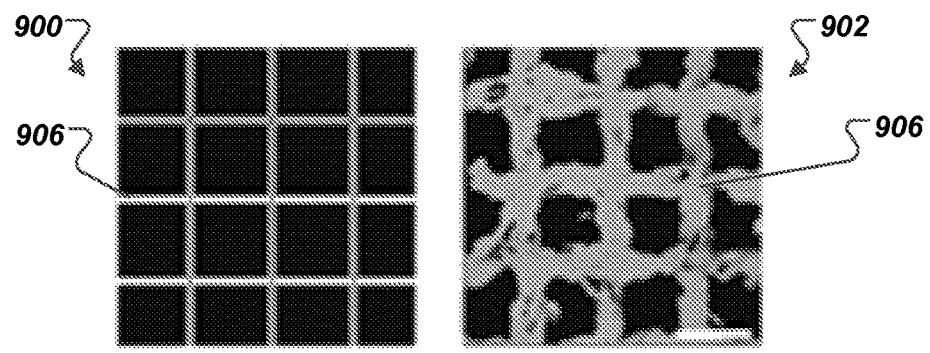
FIG. 9 shows a rectilinear pattern of filaments and fluorescence images and of the filaments at a scale.
Figure 9:
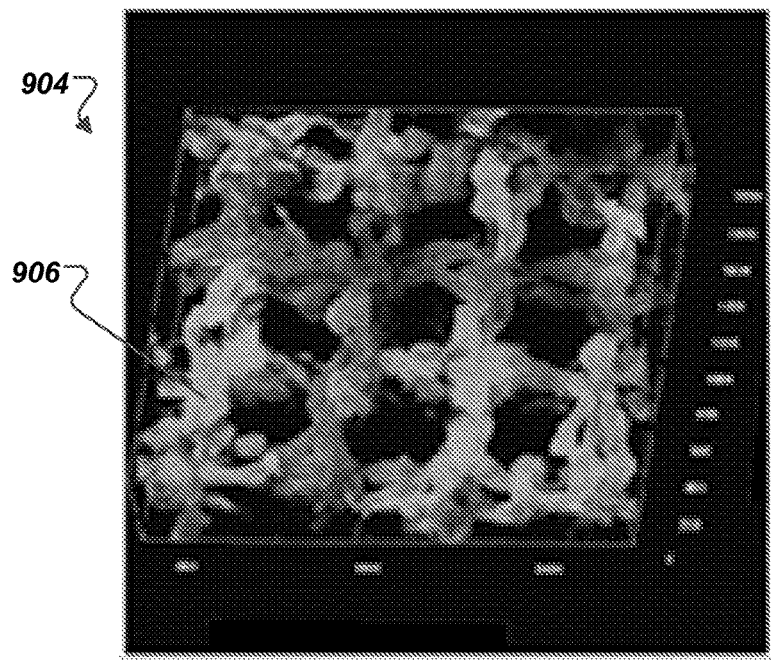
Figure 10:
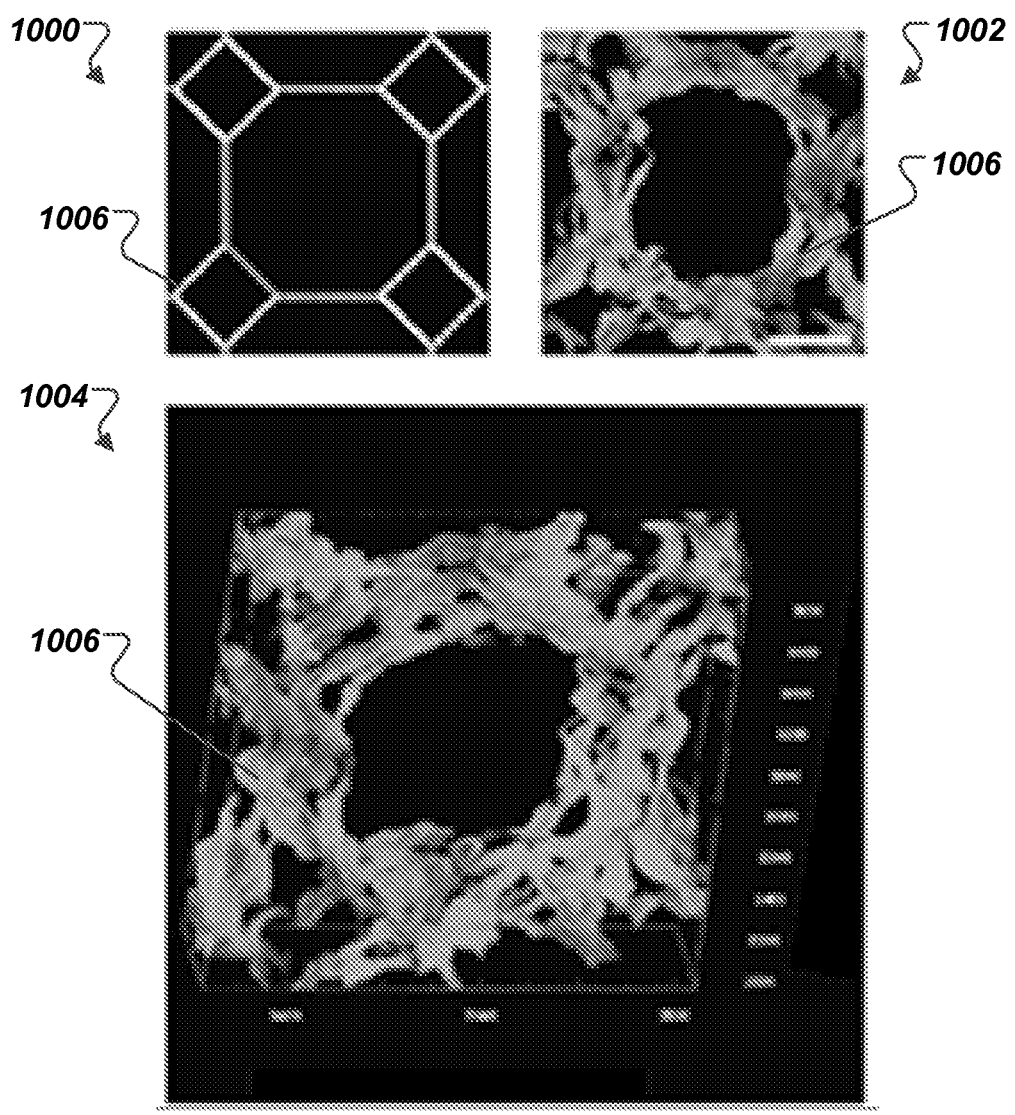
FIG. 10 shows an octagonal pattern of filaments and fluorescence images and of the filaments.

Another example of a structure that can be printed using FRESH is a filament. FIG. 8 shows a fluorescence image 800 of an alginate filament 802 embedded among gelatin particles 804 at a scale of 1 mm. FIG. 9 shows a rectilinear pattern 900 of filaments 906 and fluorescence images 902 and 904 of the filaments 906 at a scale of 500 µm. FIG. 10 shows an octagonal pattern 1000 of filaments 1006 and fluorescence images 1002 and 1004 of the filaments 1006 at a scale of 500 µm.

Figure 11:
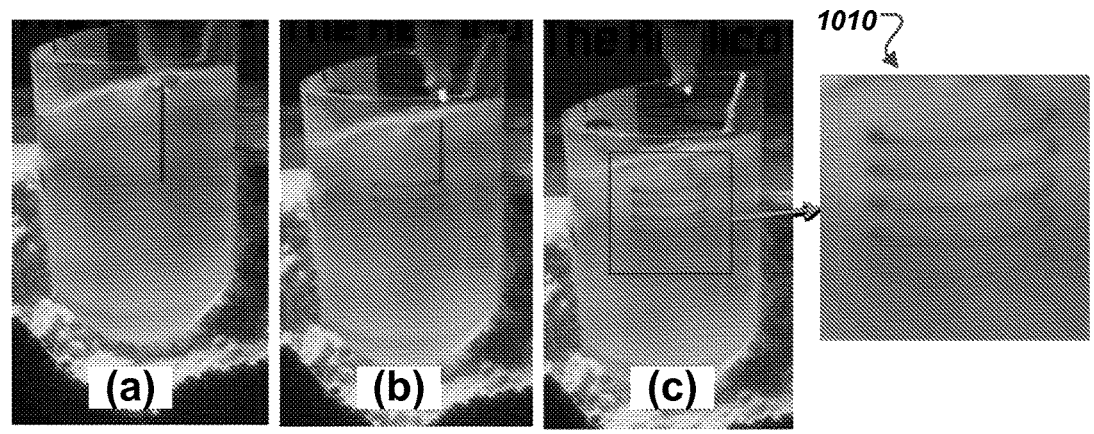
FIG. 11 shows a helix being printed at various time points (a)-(c)

Yet another example of a structure that can be printed using FRESH is a helix. FIG. 11 shows a helix 1010 being printed at various time points (a)-(c). FIG. 11 shows that FRESH can be used to print a 3D structure in any direction in 3D space, including in a non-planar fashion.

While alginate is a suitable print material for some structures, other materials may be used to print biological materials and structures. In general, alginate is not cell adhesive, and therefore may not be suitable for use in printing tissue engineering scaffold. One option is to modify the alginate with cell adhesive polypeptides of proteins. For example, alginate can be modified by the covalent linking of the arginine-glycine-aspartic acid (RGD) amino acid sequence to bind cells, or a wide range of other bioactive molecule. This may expand the utility of the alginate directly as a biomaterial and the optimal concentration of RGD-modified alginate will need to be added in order to make the printed alginate cell adhesive. The alginate can be used to facilitate gelation of other hydrogel biomaterials. Specifically, blends of alginate may be developed with both collagen type I and fibrinogen in order to develop cell adhesive scaffolds that can be remodeled by cells.

Figure 12:
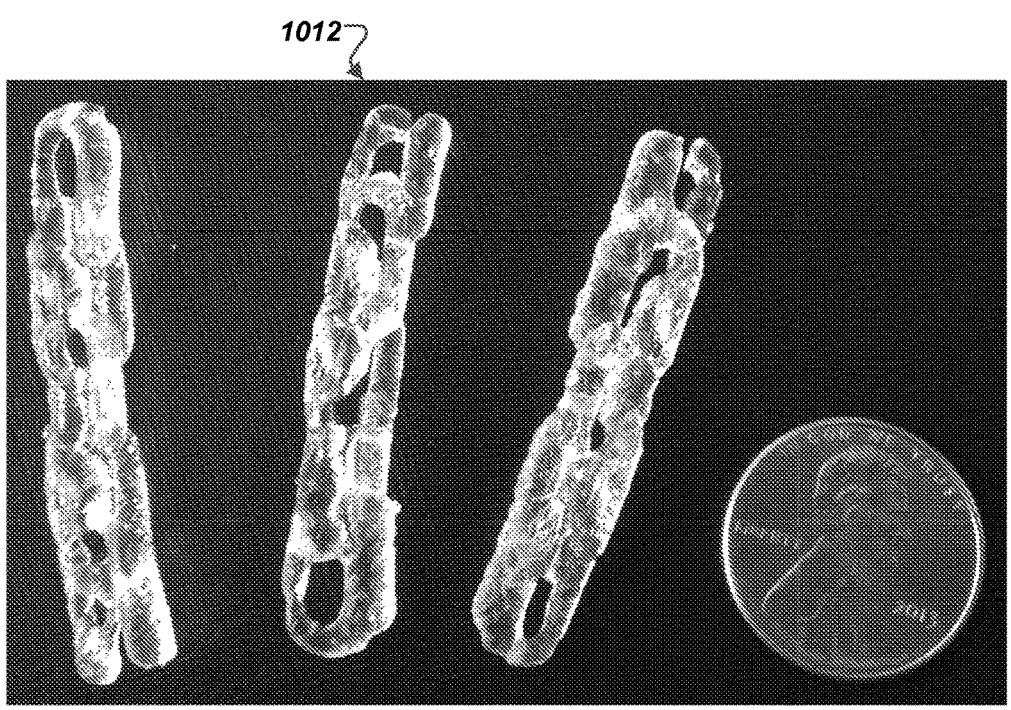
FIG. 12 shows 3D printed polydimethylsiloxane in the form of interconnected chain links.

FRESH can be used to 3D print PDMS. The PDMS is printed as a liquid that cures over 48 hours. FIG. 12 shows 3D printed PDMS in the form of interconnected chain links 1012.

FRESH demonstrates the application of fused deposition principles to the 3D printing of a gelling polymer. It utilizes widely-available open-source software and hardware to create a functional gel-prototyping system with true freeform fabrication capabilities. Gelatin slurry is a biocompatible, inexpensive, and readily available Bingham Plastic which liquefies just below human body temperature. Initial prints using the present invention can be done with food-grade gelatin powder retrieved from various grocery stores. Alginate is a biocompatible, inexpensive, readily available, and reversible material for cell-encapsulation. Alginate can also support the gelation of major biopolymers such as collagen and fibrin. Thus, FRESH may enable true freeform fabrication of any gelling biopolymer. Any biopolymer like collagen can be mixed and FRESH-printed with alginate; the alginate can be removed to reveal a collagen print. FRESH can be implemented on any RepRap 3D printer. Furthermore, these printers can be modified to print complex gel structures and perfusable vascular models with biocompatible materials.

Figure 13:
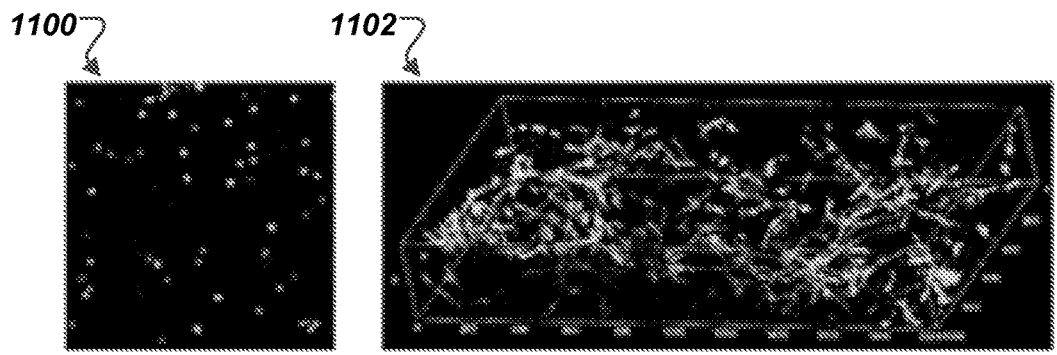
FIG. 13 shows an image and a 3D representation of C2C12 cells printed in Collagen I gel.
Figure 14:
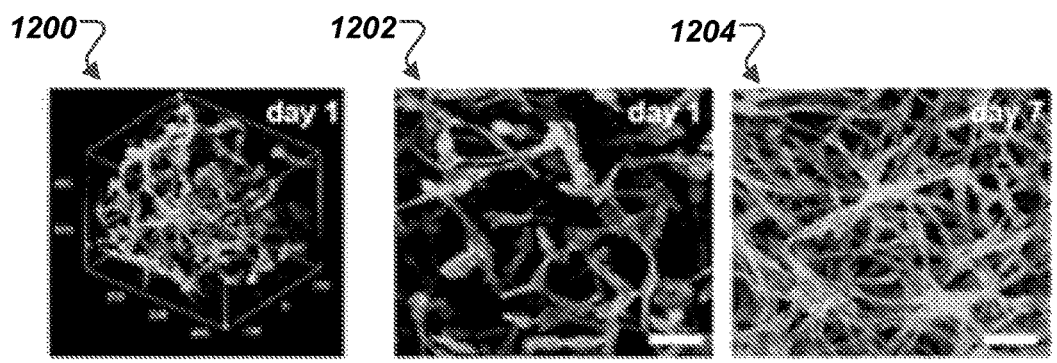
FIG. 14 shows 3D representations of C2C12 myoblasts in a collagen construct.
Figure 15:
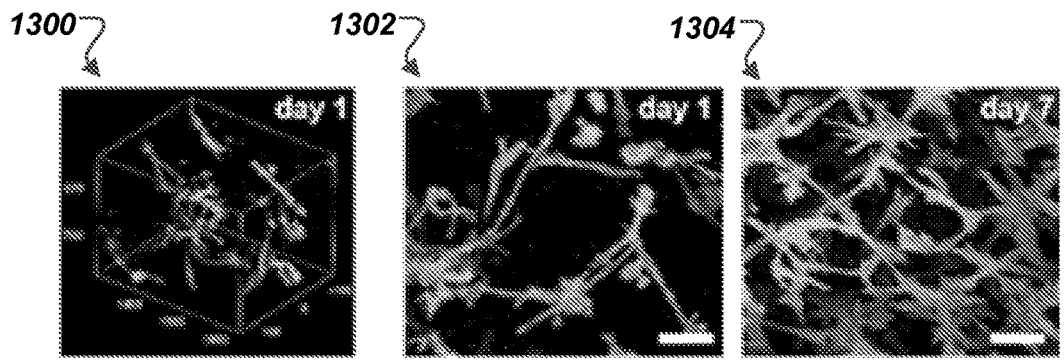
FIG. 15 shows 3D representations of MC3T3 fibroblasts in a collagen construct.

FRESH is designed to enable rapid tissue prototyping and foster widespread iterative improvements to engineered tissue designs. FRESH is capable of 3D printing any hydrophilic gel as long as it can be confined by a mechanism such as diffusion limiting. The gelatin support slurry can be combined with cell growth medium and gelling biopolymers such as collagen and fibrin, and Matrigel can be printed with cells to effectively 3D print living tissues. In one example, live-dead assays demonstrate high cell viability during FRESH printing with Collagen I and C2C12 cells. FIG. 13 shows an image 1100 and a 3D representation 1102 of C2C12 cells printed in Collagen I gel. Image 1100 shows the concentration of cells 2 hours after printing. The 3D representation 1102 shows the concentration of cells in the collagen construct 24 hours after printing. As seen in the 3D representation 1102, the cells attach and spread throughout the printed collagen construct. FIG. 14 shows 3D representations 1200, 1202, 1204 of C2C12 myoblasts in a collagen construct. The 3D representations 1200 and 1202 show the concentration of cells after 24 hours of incubation, and the 3D representation 1204 shows the concentration of cells after 7 days of incubation. The 3D representations 1202 and 1204 are shown at a scale of 50 μm. FIG. 15 shows 3D representations 1300, 1302, 1304 of MC3T3 fibroblasts in a collagen construct. The 3D representations 1300 and 1302 show the concentration of cells after 24 hours of incubation, and the 3D representation 1304 shows the concentration of cells after 7 days of incubation. The 3D representations 1302 and 1304 are shown at a scale of 50 μm. The 3D representations of the cells in the collagen constructs show that cells spread quickly and reach high density as the tissue compacts and the cells multiply. Because a tissue printed using FRESH can be released by placement in an incubator running at 37° C., FRESH essentially represents a two-step solution for rapidly prototyping tissues. Open-source frameworks for cell incubation are actively being developed, and a one-step print-and-incubate Rapid Tissue Prototyping machine is plausible.

Figure 16:
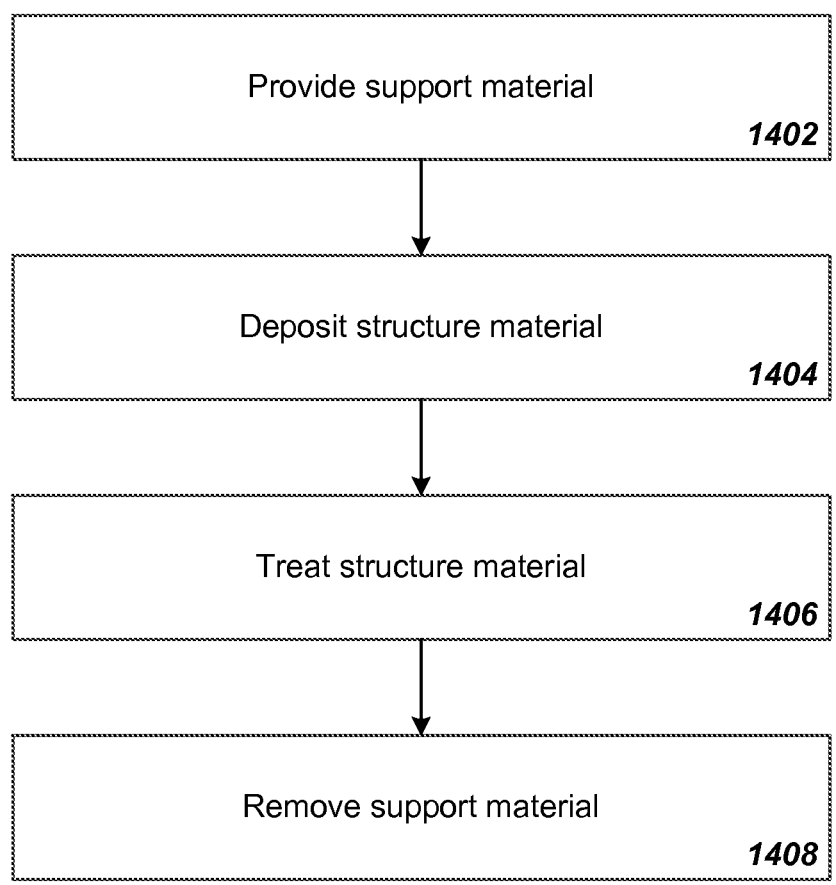
FIG. 16 is a flowchart of a process for fabricating a multidimensional structure.

FIG. 16 is a flowchart of a process 1400 for fabricating a multidimensional structure. Briefly, the process 1400 includes providing support material within which the structure is fabricated (1402); depositing, into the support material, structure material to form the fabricated structure (1404); treating the structure material to cause the structure material to transition from the fluid to the solid or semi-solid state after the deposition of the structure material (1406); and removing the support material to release the fabricated structure from the support material (1408). The process 1400 will now be described in the context of FRESH printing alginate scaffolds in a gelatin slurry bath. However, other suitable materials may be used instead of alginate and gelatin.

A support material, such as a gelatin slurry bath, is provided (1402). To create the gelatin slurry bath, 30 grams of gelatin may be hydrated in excess 7 mM $CaCl_2$ at 4° C. The slurry may be blended with a blender for 60 seconds in a 500 mL mason jar and centrifuged at 1400 rpm for 3 minutes. Slurry supernatant may be aspirated and replaced with 7 mM $CaCl_2$ at 20° C. The slurry may be resuspended by vortexing. This washing procedure may be repeated two additional times, except the gelatin slurry is not replenished with 7 mM $CaCl_2$ the final time. Washed slurry may be loaded into 60 mm diameter glass petri dishes to be used for FRESH prints.

The structure material may be a solution of fluorescent alginate. A solution of 2.0%-w/v Sodium Alginate, 0.02%-w/v 6-Aminofluorescein, 0.022%-w/v EDC, and 0.025% w/v Sulfo-NHS may be prepared and stirred for 48 hours at 20° C. Unreacted 6-Aminofluorescein may be removed by five consecutive 12 hr dialysis shifts against 2%-w/v Sodium Alginate at 4° C. in dialysis cassettes.

Before printing, a standard 3 mL syringe with a 0.25 mm-ID stainless steel nozzle may be filled with a solution of 0.08%-w/v fluorescein-labeled alginic acid and 1.92% w/v Sodium Alginate and loaded onto a custom-modified Replicator 3D Printer. Digital models of the alginate scaffolds may be created using, for example, SolidWorks and MeshLab softwares. Alginate scaffolds were printed in the gelatin slurry bath at 20° C. (1404), heated to 37° C. (1406), and washed free from molten gelatin slurry with 0.13 M $CaCl_2$ (1408).

FRESH makes it possible to 3D print protein scaffolds within a thermally-reversible support bath that can be selectively remove once the entire scaffold is complete. Thus, FRESH can be used to engineer a variety of tissues.

Figure 17:
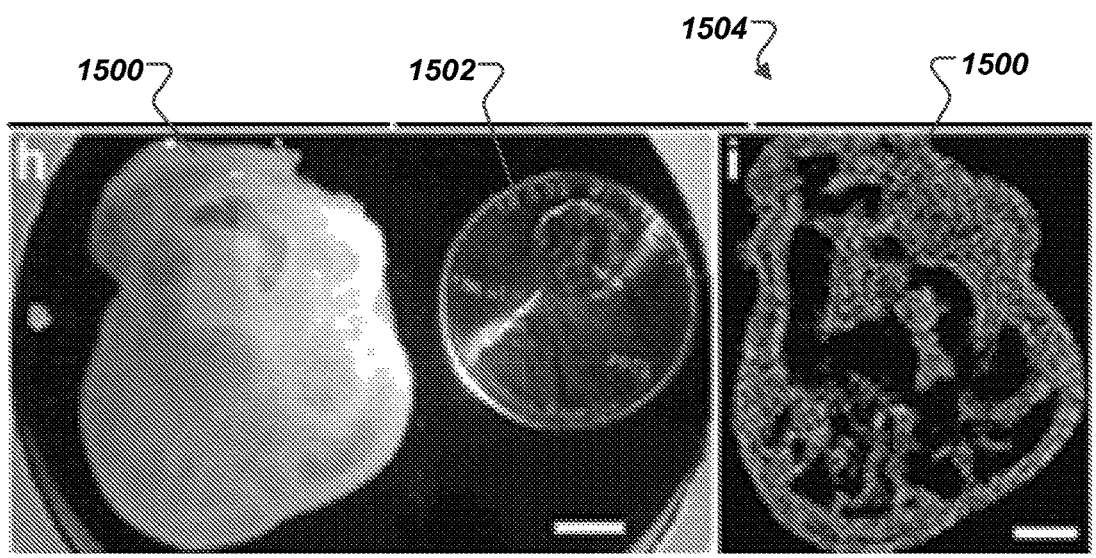
FIG. 17 shows a FRESH print of an embryonic chicken heart.

For example, FRESH can be used to engineer complex 3D heart tissue with a level of structure and functional performance that is difficult to create using alternative approaches. To 3D print anatomically-optimized engineered cardiac tissues, a 3D computer model of the neonatal human ventricle may be built based on 3D MRI scans, which enables the use of computational modeling to optimize the tissue design to maximize performance as well as optimize the design for 3D printing. An enhanced version of the FRESH 3D printing process is used that uses alginate-collagen blends for fabricating tissue engineering scaffolds. Printing parameters to maximize cell survival and integration into the construct are optimized, making sure to match degradation rates with the formation of new muscle tissue. A 3D human heart muscle may then be engineered using human stem cell derived cardiomyocytes. FIG. 17 shows a FRESH print of an embryonic chicken heart 1500 next to a penny 1502 and a fluorescence image 1504 of a layer of the FRESH printed embryonic chicken heart 1500 at a scale of 1 cm. The fluorescence image 1504 shows the internal structures of the FRESH printed embryonic chicken heart 1500.

As another example, FRESH can be used for 3D printing of complex vasculature for repair of traumatic muscle injury. FRESH 3D bioprinting can be used in order to engineer patient-specific vascular networks for rapid regeneration of large-volume muscle defects. This vascular network may be composed of ECM proteins and serves as the scaffold to guide muscle regeneration as well as provide nutrient mass transport. FRESH can engineer patent, complex, 3D vascular networks that scale from main arteries and veins down to arterioles and venuoles, with 1 mm internal diameter. This level of structural and functional performance may be difficult to create using alternative approaches. FRESH has the capability to 3D print a high-density vascular network, which can be used to engineer large-volume skeletal muscle constructs.

FRESH can be used to engineer high-fidelity muscle tissue engineering for craniofacial repair. Fine skeletal muscles appropriate for craniofacial reconstruction following traumatic injury to the head can be engineered. For example, skeletal muscle cells can be integrated into nanostructured fibers composed of the extracellular matrix protein, such as collagen. This will result in a living cell thread composed entirely of cells and biopolymers, eliminating any synthetic polymers from the system. Skeletal myoblasts can be seeded onto collagen fibers 3D printed with FRESH, or mixed with the collagen and FRESH printed directly as cell-laden fiber to create living muscle fiber threads of highly aligned muscle cells. Once myoblasts cell fibers are created, the cells will align and fuse into myotubes. Once the living muscle fiber threads are generated with FRESH, they can be used to weave muscle tissue constructs that recapitulate the overall shape and cellular architecture of craniofacial muscles. Using custom bioreactors, support posts can be integrated into 35-mm cell culture Petri dishes around which the cell threads can be weaved. Alternatively, the posts and cell threads can be printed in the same construct. The posts can be printed from PDMS, and the tissue can be printed from collagen and cell suspensions. This would be an example of printing hybrid synthetic and living prints with complex purposes. By proper placement of these post and weaving patterns, a variety of muscle structures can be regenerated.

Figure 18:
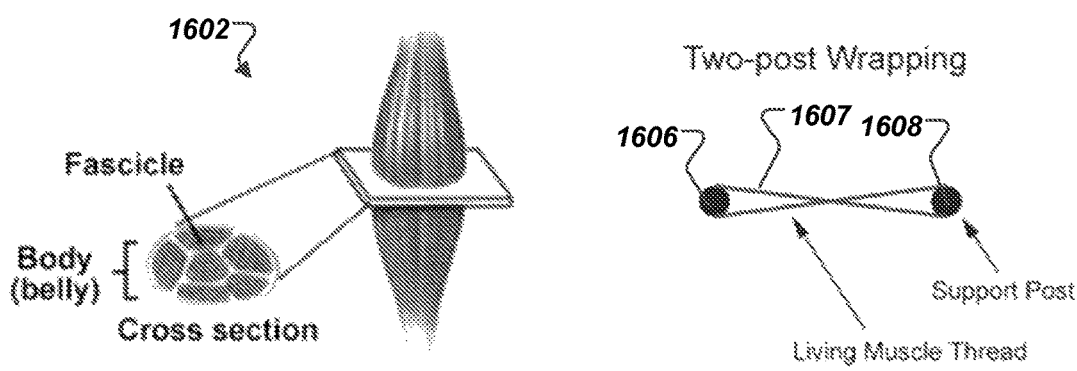
FIG. 18 illustrates weaving used to regenerate various muscle structures using the living muscle fiber threads.
Figure 18:
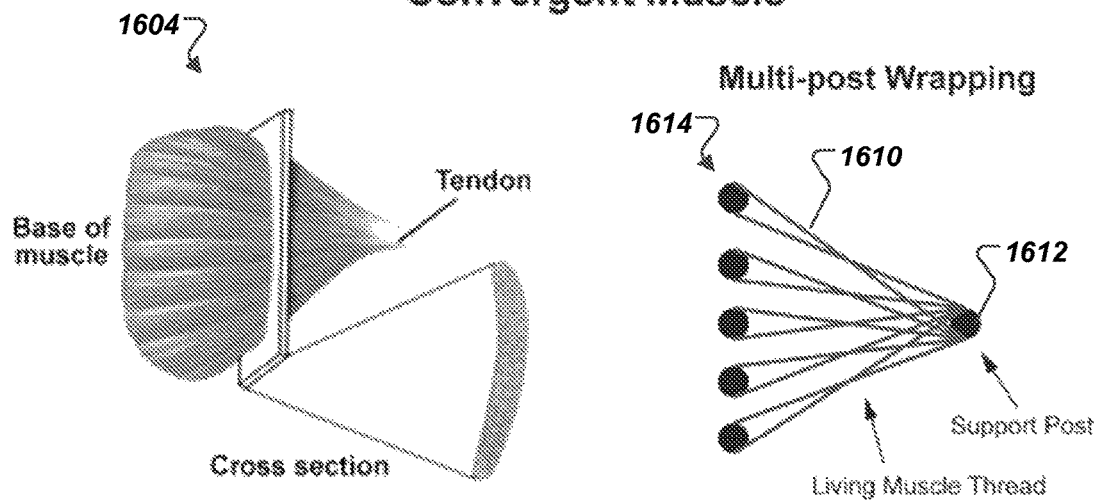

FIG. 18 illustrates weaving used to regenerate various muscle structures using the living muscle fiber threads. FRESH provides the capability to regenerate both parallel muscle tissue types 1602 and convergent muscle tissue types 1604. Parallel muscles 1602 have a spindle shape and circular cross-section with all muscle cells aligned in the same, uniaxial direction. To recreate this structure, the living muscle fiber thread 1607 is wrapped back-and-forth between to support posts 1606 and 1608. Convergent muscles 1604 have more of a fan shape corresponding cross-section that is thin and wide. To recreate this structure, the living muscle fiber thread 1610 is wrapped around one post 1612 on the right and then a tightly spaced column of posts 1614 on the left. Alternatively, FRESH can be used to print the muscle fibers directly into the parallel and convergent muscle structures with or without the support posts. Other muscle structures that can be engineered using FRESH include circular muscle bundles such as sphincters appropriate for repair of the orbicularis oculi muscle around the eye, and the orbicularis oris muscle around the mouth.

A number of implementations have been described. Nevertheless, various modifications can be made without departing from the spirit and scope of the processes and techniques described herein. In addition, the processes depicted in the figures do not require the particular order shown, or sequential order, to achieve desirable results. In addition, other steps can be provided, or steps can be eliminated, from the described processes, and other components can be added to, or removed from, the describe apparatus and systems. Accordingly, other embodiments are within the scope of the following claims.

What is claimed is:

1. A method for fabricating a structure having at least two dimensions, the method comprising:
   providing support material within which the structure is fabricated;
   wherein the provided support material is stationary at an applied shear stress level below a threshold shear stress level and flows at an applied shear stress level at or above the threshold shear stress level during fabrication of the structure; and
   wherein the provided support material is configured to mechanically support at least a portion of the structure and to prevent deformation of the structure during the fabrication of the structure;
   depositing, into the support material, structure material to form the fabricated structure, wherein the depositing comprises applying a shear stress level above the threshold shear stress level to a portion of the support material;
   wherein the deposited structure material is suspended in the support material at a location where the structure material is deposited; and
   wherein the structure material comprises a fluid that transitions to a solid or semi-solid state after deposition of the structure material; and
   removing the support material to release the fabricated structure from the support material.

2. The method of claim 1, wherein the support material comprises a gel material.

3. The method of claim 1, wherein the support material comprises a hydrogel material.

4. The method of claim 1, wherein the support material comprises micronized particulates.

5. The method of claim 1, wherein the support material comprises a thermo-reversible material.

6. The method of claim 1, wherein the structure material comprises a material having an elastic moduli of less than 1 megapascal.

7. The method of claim 1, wherein the structure material comprises at least one of a gel material that is different from the support material, a metal material, a ceramic material, or a polymer material.

8. The method of claim 1, wherein the structure material comprises at least one of an alginate material, a collagen material, a fibrin material, a hyaluronic acid material, a protein material, a polysaccharide hydrogel material, synthetic gel material, an elastomer polymer material, a rigid polymer material, or a polydimethylsiloxane (PDMS) elastomer.

9. The method of claim 1, wherein the structure material is deposited using a syringe-based extruder that is inserted into the support material and extrudes the structure material into the support material.

10. The method of claim 1, further comprising:
    treating the structure material to cause the structure material to transition from the fluid to the solid or semi-solid state after the deposition of the structure material.

11. The method of claim 10, wherein the support material comprises a crosslinking agent for treating the structure material to cause the structure material to transition from the fluid to the solid or semi-solid state after the deposition of the structure material.

12. The method of claim 11, wherein the crosslinking agent comprises at least one of calcium chloride or thrombin.

13. The method of claim 10, wherein the support material comprises a material having a different pH from the structure material for treating the structure material to cause the structure material to transition from the fluid to the solid or semi-solid state after the deposition of the structure material.

14. The method of claim 10, wherein treating the structure material comprises heating the structure material.

15. The method of claim 10, wherein treating the structure material comprises cooling the structure material.

16. The method of claim 10, wherein treating the structure material comprises radiating the structure material with ultraviolet light.

17. The method of claim 1, wherein removing the support material comprises heating the support material.

18. The method of claim 1, wherein removing the support material comprises cooling the support material.

19. The method of claim 1, wherein removing the support material comprises removing cations to disrupt crosslinking of the support material.

20. The method of claim 1, wherein the fabricated structure is a biological tissue or a tissue engineering scaffold.

21. The method of claim 1, wherein depositing, into the support material, the structure material to form the fabricated structure comprises:

depositing the structure material layer by layer in an XY plane.

22. The method of claim 1, wherein depositing, into the support material, the structure material to form the fabricated structure comprises:

depositing the structure material layer by layer in an XZ plane.

23. The method of claim 1, wherein depositing, into the support material, the structure material to form the fabricated structure comprises:

depositing the structure material in a non-planar configuration.

24. The method of claim 1, wherein the fabricated structured has three-dimensions, and wherein the fabricated structure has printed anisotropic mechanical properties in a direction that lie in a XY plane.

25. A method for fabricating a tissue scaffold, the method comprising:

performing a printing operation at approximately twenty degrees Celsius, the printing operation comprising:

providing a gelatin slurry support bath within which the tissue scaffold is fabricated;

wherein the gelatin slurry support bath flows in a presence of an applied shear force and transforms into a non-flowing fluid in an absence of the applied shear force;

extruding, from a nozzle, a hydrogel into the gelatin slurry support bath to form the tissue scaffold, with the hydrogel having an elastic moduli of less than 1,000 kilopascal;

wherein the nozzle applies a shear force to a portion of the gelatin slurry support bath;

wherein the gelatin slurry support bath includes calcium chloride to provide divalent cations to crosslink the hydrogel as the hydrogel is extruded out of the nozzle; and wherein the gelatin slurry support bath is configured to mechanically support the hydrogel and to prevent deformation of the hydrogel during printing of the tissue scaffold; and placing the gelatin slurry support bath with the extruded hydrogel into an incubator that is heated to approximately thirty-seven degrees Celsius to melt the gelatin slurry support bath and to release the tissue scaffold.

26. The method of claim 25, wherein the hydrogel comprises at least one of alginate, collagen type I, fibrin, or hyaluronic acid.

27. The method of claim 25, wherein the hydrogel comprises a cell laden hydrogel.

* * * * *